(12) United States Patent
Lane

(10) Patent No.: US 7,021,314 B1
(45) Date of Patent: Apr. 4, 2006

(54) STOMA STENT WITH INTEGRATED SPEECH FLAP VALVE

(76) Inventor: Charles J. Lane, 181 Lake Shore Dr., Duxbury, MA (US) 02332

( * ) Notice: Subject to any disclaimer, the term of this patent is extended or adjusted under 35 U.S.C. 154(b) by 0 days.

(21) Appl. No.: 10/894,934

(22) Filed: Jul. 19, 2004

(51) Int. Cl.
*A61M 16/00* (2006.01)

(52) U.S. Cl. ............... 128/207.29; 128/200.26; 128/207.16

(58) Field of Classification Search ......... 128/200.26, 128/207.16, 207.29, 912; 623/9
See application file for complete search history.

(56) References Cited

U.S. PATENT DOCUMENTS

| | | | |
|---|---|---|---|
| 2,039,142 A * | 4/1936 | Brehm ............... 128/207.17 |
| 3,137,299 A * | 6/1964 | Tabor ............... 128/207.16 |
| 3,263,684 A * | 8/1966 | Bolton ............... 128/207.16 |
| 3,628,565 A | 12/1971 | McWethy | |
| 3,844,290 A * | 10/1974 | Birch et al. ............. 128/207.16 |
| 3,952,335 A * | 4/1976 | Sorce et al. ............... 623/9 |
| 3,957,046 A | 5/1976 | Harris | |
| 4,040,428 A * | 8/1977 | Clifford ............... 128/207.16 |
| 4,435,853 A * | 3/1984 | Blom et al. ............... 623/9 |
| 4,439,872 A | 4/1984 | Henley-Cohn et al. | |
| 4,538,607 A * | 9/1985 | Saul ............... 128/207.16 |
| 4,582,058 A * | 4/1986 | Depel et al. ............. 128/207.17 |
| 4,610,691 A | 9/1986 | Depel et al. | |
| 4,614,516 A | 9/1986 | Blom et al. | |
| 4,759,356 A * | 7/1988 | Muir ............... 128/207.16 |
| 4,809,693 A * | 3/1989 | Rangoni et al. ........ 128/207.16 |
| 4,820,304 A * | 4/1989 | Depel et al. ............... 623/9 |
| 4,911,716 A | 3/1990 | Biom et al. | |
| 4,971,054 A * | 11/1990 | Andersson et al. .... 128/207.16 |
| 5,048,518 A * | 9/1991 | Eliachar et al. ........ 128/207.14 |
| 5,059,208 A * | 10/1991 | Coe et al. ............... 623/9 |
| 5,107,828 A * | 4/1992 | Koss et al. ............ 128/200.26 |
| 5,259,378 A | 11/1993 | Huchon et al. | |
| 5,287,852 A | 2/1994 | Arkinstall | |
| 5,314,470 A | 5/1994 | Persson | |
| 5,391,205 A * | 2/1995 | Knight ............... 623/9 |
| 5,392,775 A * | 2/1995 | Adkins et al. ........ 128/207.16 |
| 5,472,123 A | 12/1995 | Jangaard | |
| 5,480,432 A * | 1/1996 | Suding et al. ............ 623/9 |
| 5,578,083 A * | 11/1996 | Laguette et al. ............ 623/9 |
| 5,683,458 A | 11/1997 | Urken | |
| 5,693,097 A | 12/1997 | Laguette et al. | |
| 5,935,165 A | 8/1999 | Schouwenburg | |
| 6,189,534 B1 | 2/2001 | Zowtiak et al. | |
| 6,206,251 B1 | 3/2001 | Williams | |
| 6,230,940 B1 | 5/2001 | Manning et al. | |
| 6,439,233 B1 * | 8/2002 | Geertsema ............. 128/207.16 |
| 6,789,542 B1 * | 9/2004 | Bischoff ............... 128/207.16 |
| 6,802,316 B1 * | 10/2004 | Fulgham ............... 128/207.14 |

* cited by examiner

*Primary Examiner*—Aaron J. Lewis
(74) *Attorney, Agent, or Firm*—John P. McGonagle

(57) ABSTRACT

A stoma stent with an internal, self-contained flap valve permitting speech. The one-way flap valve is part of the stent.

1 Claim, 2 Drawing Sheets

STOMA STENT WITH INTEGRATED SPEECH FLAP VALVE

BACKGROUND OF THE INVENTION

This invention relates to a tracheal device which permits a patient to breath after a tracheotomy, and in particular, to a stoma stent with an integrated speech flap valve.

A tracheotomy is a surgical operation in which an incision, or opening, is cut through the front of the neck and into the trachea, or windpipe. A tracheotomy creates an alternate passage to the lungs for air that cannot flow from the nose and mouth through the trachea because of an obstruction. Obstructions may occur when a foreign body lodges in the larynx, or voice box, above the trachea; as a result of swelling or spasm of the larynx or vocal cords; or from infection and swelling of the epiglottis, the thin flap of cartilage covering that keeps food and liquid out of the trachea.

After a patient has undergone a tracheotomy, he is often provided with a tubular prosthesis, e.g., a short stationary tube, including air channel means between the trachea and the outside ambient air. A tracheotomy that includes the insertion of a tubular prosthesis into the trachea is called a tracheostomy. The purpose of a tracheostomy is to keep the airway from closing prematurely and to enable the physician to take further measures, if necessary, to ensure that the patient has a patent airway. The prosthesis is held in place in the stoma so that it may be used for long time periods, maintaining patentcy of the tracheostomy. Such prosthesis are known as stoma stents.

A tracheostomy prevents patients from using their vocal cords. Once the reason for having a tracheostomy has ended, the tracheostomy is closed and patients are able to breathe and speak normally. However, in some situations, a tracheostomy must remain in place for a period of time, often lengthy. This presents a particular physiological problem associated with prior art stents in that a patient with an open stent cannot use his vocal cords to speak.

Human speech is enabled by the passage of expired air from the lungs up though the trachea, passing through the laryngeal cavity and exhaled through the mouth. The laryngeal cavity contains a plurality of adjustable-tensioned mucous membranes, or vocal cords, stretched across the cavity. During such exhalation, these membranes are cause to vibrate and produce audible sounds by a flow of expired air, and differences in pitch are achieved by muscles which adjust the tension of these vibratory membranes.

With some stents one-way speech valves are offered as an accessory to the device. The valves close during exhalation thereby forcing air through the laryngeal cavity out through the mouth. During inhalation, the valves open bringing air in through the stent. These valves are designed to allow a patient to speak without physically occluding the stoma opening. With some prior art stents one-way valves are inserted into the stent. While these work, they also reduce air flow. Other types of valves are fitted over the stent and extend well beyond the stoma site. The added weight may require the stent to be tied in place.

SUMMARY OF THE INVENTION

The present invention is a stoma stent with an internal, self-contained flap valve permitting speech. The stoma stent maintains a stoma site and eliminates the need for a tracheotomy tube. The stoma stent is easily removed by a patient, cleaned and replaced.

The present invention addresses the problem of prior art devices by providing a one-way flap valve as part of the stent. As part of the stent itself, air flow through the stent is not reduced. The stent of the present invention also has minimal external protrusions.

These together with other objects of the invention, along with various features of novelty which characterize the invention, are pointed out with particularity in the claims annexed hereto and forming a part of this disclosure. For a better understanding of the invention, its operating advantages and the specific objects attained by its uses, reference should be had to the accompanying drawings and descriptive matter in which there is illustrated a preferred embodiment of the invention.

DETAILED DESCRIPTION OF INVENTION

Figure 1:
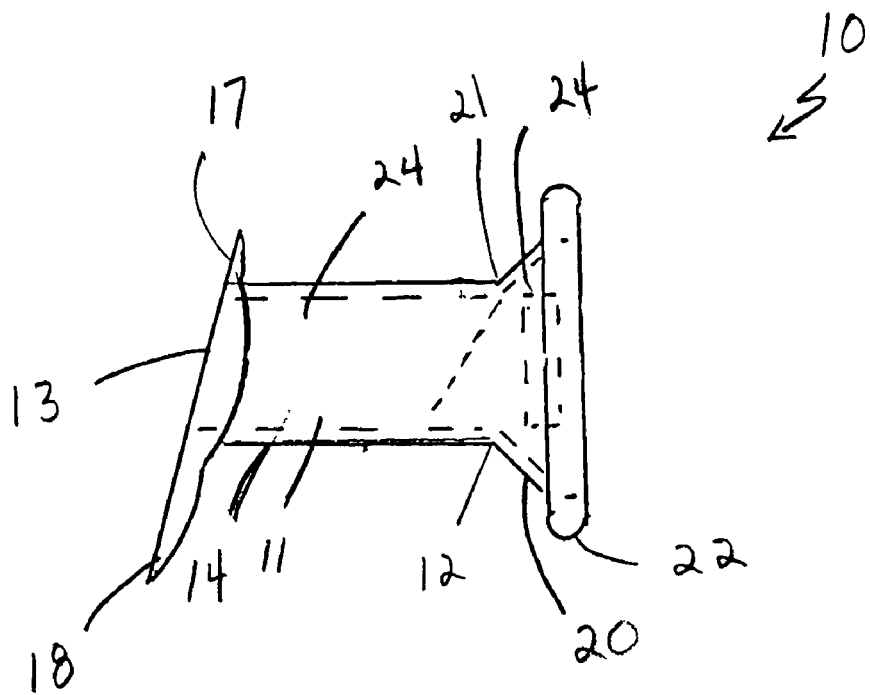
FIG. 1 is a side elevational view of a stoma stent in accordance with the present invention.
Figure 2:
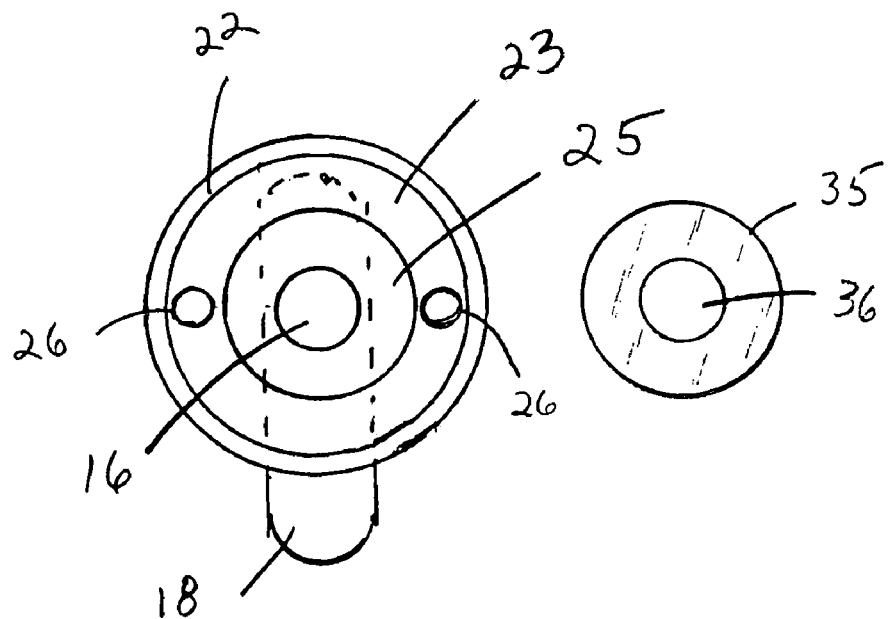
FIG. 2 is a proximal end view of the invention.
Figure 3:
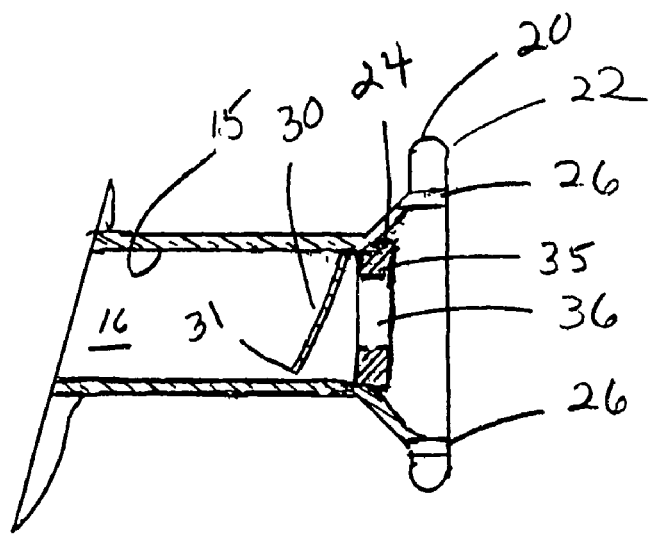
FIG. 3 is a cross-sectional view of the invention embodiment illustrated in FIG. 1.
Figure 4:
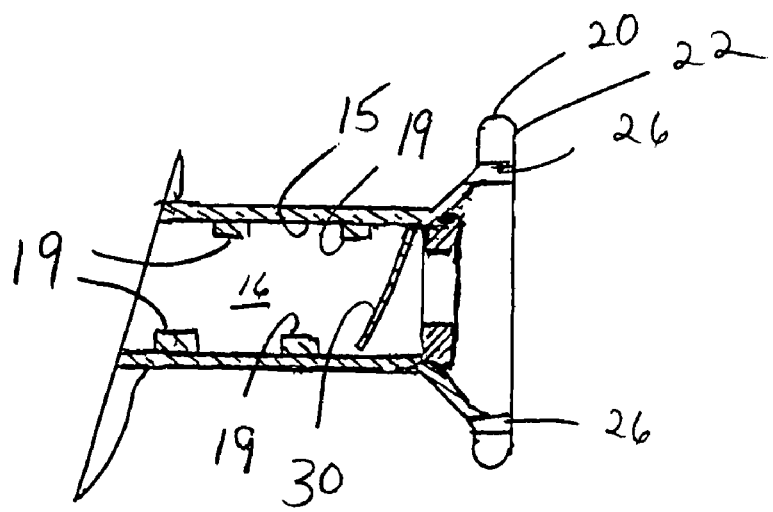
FIG. 4 is a cross-sectional view as shown in FIG. 4 with baffles added thereto.

Referring to the drawings in detail wherein like elements are indicated by like numerals, there is shown a stoma stent 10 constructed according to the principles of the present invention. The stoma stent 10 has a hollow tube 11 having an open first end 12 and an opposite open second end 13, said first end 12 and second end 13 defining a tube longitudinal axis. In the embodiment shown, the tube 11 is straight. In other embodiments, the tube 11 may be curvilinear to conform to the anatomical needs of a tracheotomy incision. The tube 11 has a smooth exterior surface 14 and smooth interior surface 15, said interior surface 15 defining a tube interior 16. The tube second end 13 has a pair of angled flanges 17, 18 extending radially outward from the tube exterior surface 14 away from a tube central longitudinal axis. The tube open first end 12 terminates in a frusto-conic forward portion 20, said tube open first end 12 and forward portion 20 forming a junction 21 with an initial diameter matching the diameter of the tube 11. The forward portion 20 expands forwardly and outwardly terminating in a rounded rim 22, said rim 22 defining a stent proximal end. Said forward portion 20 has a longitudinal central axis coincident with the longitudinal central axis of the tube 10. In the embodiment shown, the diameter of the stent proximal end 22 is approximately twice the diameter 21 of the tube 11. The tube second end 13 defines a stent distal end.

The tube interior 16 has a circular, thin flap 30 molded directly to the tube interior surface 15, said flap 30 having a diameter slightly less than the diameter of the tube interior 16, said flap 30 being radially connected along a portion of its perimeter 31 to the tube interior surface 15 adjacent to the tube first end 12. The flap 30 is nominally positioned so that in a closed position the planes of its surfaces are transverse to the longitudinal axis of the tube 11. In another embodiment of the invention, the flap 30 may be nominally positioned so that in a closed position the planes of its surfaces are at an acute angle to the longitudinal axis of the tube 11. The flap 30 is adapted to be in a closed position during patient exhalation and in an open position during inhalation.

The forward portion 20 has an inner surface 23 and an outer surface 24. The forward portion inner surface 23 has a channel 25 formed therein adjacent to the junction 21. A retaining ring 35 is inserted into the channel 25 and bonded into place. The ring inner opening 36 has a diameter slightly less than the diameter of the tube interior 16. The retaining ring 35 provides a locking detent for the flap 30 during exhalation.

After a tracheostomy, the stoma stent 10 may be inserted into the stoma, i.e. opening between the trachea and outside, with the stent distal end 13 disposed through the incision into the trachea, and the stent forward portion 20 disposed outside and partially into the incision. The frusto-conic shape of the forward portion 20 provides a slidable fit, and thereby a seal, against the patient's neck. The forward portion 20 may optionally have two opposed holes 26 formed therein near to the rim 22. The forward portion holes are adapted to hold cotton ties (not shown).

In another embodiment of the invention, baffles may be installed in the tube interior 16, said baffles being comprised of a plurality of staggered posts 19 attached to the tube interior surface 15. The internal baffles 19 prevent the flap 30 from being ingested if the flap 30 should break free from the tube.

It is understood that the above-described embodiment is merely illustrative of the application. Other embodiments may be readily devised by those skilled in the art which will embody the principles of the invention and fall within the spirit and scope thereof.

I claim:

1. A stoma stent for a tracheostomy, comprising:
   a hollow tube having an open first end, an opposite open second end, a smooth exterior surface and smooth interior surface, said interior surface defining a tube interior, said first end and second end defining a tube longitudinal axis;
   a pair of angled flanges at the tube second end extending radially outward from the tube exterior surface away from a tube central longitudinal axis;
   a frusto-conic forward portion having an inner surface and an outer surface, said forward portion being joined to said tube open first end, said tube open first end and forward portion forming a junction with an initial diameter matching an inner diameter of the tube, said forward portion expanding forwardly and outwardly and terminating in a rounded rim, said rim defining a stoma stent proximal end, said forward portion having a longitudinal central axis coincident with the longitudinal central axis of the tube, wherein the tube second end defines a stent distal end;
   a circular, thin flap within said tube interior joined directly to the tube interior surface, said flap having a diameter slightly greater than the diameter of the tube interior, said flap having a perimeter and being radially connected along a portion of said perimeter to the tube interior surface adjacent to the tube first end, said flap adapted to being in a closed position transverse to the longitudinal axis of said tube during patient exhalation and in an open position during inhalation;
   a radial channel formed in the forward portion inner surface adjacent to the junction;
   a retaining ring adapted to being inserted into the channel, said ring having an inner opening with a diameter slightly less than the diameter of the tube interior, said retaining ring providing a locking detent for the flap during exhalation;
   two opposed holes formed in said forward portion near to the rim; and
   a plurality of baffles in the tube interior, said baffles being comprised of a plurality of staggered posts attached to the tube interior surface.

* * * * *